United States Patent [19]

Avallone et al.

US005318556A

[11] Patent Number: 5,318,556
[45] Date of Patent: Jun. 7, 1994

[54] FLUID BAG

[75] Inventors: John M. Avallone, Providence, R.I.; Michael A. Valerio, Wrentham, Mass.

[73] Assignee: Deknatel Technology Corporation, Wilmington, Del.

[21] Appl. No.: 44,670

[22] Filed: Apr. 9, 1993

[51] Int. Cl.$^5$ .............................................. A61B 19/00
[52] U.S. Cl. .................................... 604/410; 604/403; 604/416
[58] Field of Search .............. 128/D12; 604/118, 131, 604/132, 133, 141, 142, 145-147, 403, 410

[56] References Cited

U.S. PATENT DOCUMENTS

| Re. 27,132 | 6/1971 | Ilg . | |
|---|---|---|---|
| 2,766,907 | 10/1956 | Wallace, Jr. | 128/DIG. 12 |
| 3,054,401 | 9/1962 | Gewecke . | |
| 3,228,395 | 1/1966 | Gewecke . | |
| 3,335,912 | 8/1967 | Reeves, Jr. . | |
| 3,399,040 | 8/1968 | Ilg . | |
| 3,888,239 | 6/1975 | Rubinstein . | |
| 4,041,944 | 8/1977 | Rhodes . | |
| 4,270,533 | 6/1981 | Andreas | 128/DIG. 12 |
| 4,337,769 | 7/1982 | Olson . | |
| 4,564,359 | 1/1986 | Rühland . | |
| 4,573,992 | 3/1986 | Marx . | |
| 4,798,578 | 1/1989 | Ranford . | |
| 4,976,707 | 12/1990 | Bodicky et al. . | |
| 5,074,839 | 12/1991 | Choksi et al. . | |

FOREIGN PATENT DOCUMENTS 2006054  2/1970  Fed. Rep. of Germany .

OTHER PUBLICATIONS

Product Brochure, "Pleur-evac © Plus A-9250", Deknatel, Inc., Printed in USA, Sep. 1992.

Primary Examiner—Randall L. Green
Assistant Examiner—P. Zuttarelli
Attorney, Agent, or Firm—Pennie & Edmonds

[57] ABSTRACT

A bag for transferring fluid from a source of fluid to a fluid delivery system including three sheets of flexible material joined to form first and second adjacent compartments. Fluid is transferred into the first compartment via a perforated tube connected to the fluid source at a first end. The tube extends into the first compartment and is further connected to the fluid delivery system at a second end. The second compartment may be selectively inflated to exert force on the first compartment and control the rate of fluid flow through the tube to the delivery system.

11 Claims, 4 Drawing Sheets

FLUID BAG

The invention generally relates to transfer bags, and in particular, to a fluid transfer bag for selectively delivering fluids under pressure.

BACKGROUND OF THE INVENTION

Reinfusion systems are commonly used to collect and infuse shed blood in post-operative situations. Typically, such reinfusion systems comprise a device, such as a canister equipped to collect shed blood and reinfuse blood through a separate orifice. The blood collected is reinfused directly to a patient from the system through a catheter or needle.

These reinfusion systems are somewhat limited in the rate at which the collected blood may be reinfused to a patient. In the known reinfusion systems described above, safety and practicality issues dictate that collected blood may be reinfused only as quickly as gravity permits. In addition, as the collected blood is reinfused through a needle or catheter, the blood flow can be restricted considerably, further slowing the rate at which reinfusion occurs. The systems are further limited in capacity. In particular, the amount of blood which can be collected and reinfused is limited by the size of the collection chamber within the canister. Further, as blood is aspirated from the wound site faster than it can be reinfused to the patient, the volume of the collection chamber is quickly filled to capacity.

SUMMARY OF THE INVENTION

The present invention provides an apparatus for collecting and transferring fluid therefrom comprising a first expandable compartment for containing at least a portion of the fluid to be collected and transferred. The apparatus includes fluid means for allowing fluid to flow selectably into and out from the chamber and includes at least one perforation in fluid communication with the first compartment. The apparatus further comprises means for changing the pressure of the fluid in the first compartment, wherein the pressure changing means exerts force on at least a portion of the exterior surface of the first compartment to aid in regulating the flow of the fluid through the fluid means. The fluid means preferably comprises a tube having a plurality of perforations in fluid communication with the first compartment. The pressure changing means preferably comprises a second expandable compartment adjacent the first expandable compartment. The apparatus preferably further comprises pressure source means in communication with the second compartment.

In accordance with another aspect of the invention, a fluid transfer bag comprises first and second sheets joined along edges thereof to define outer wall of the bag. A third sheet is disposed between the first and second sheets and joined to at least portions of the second sheet, wherein the third sheet separates the space defined between the first and second outer sheets into a first expandable compartment and a second expandable compartment, the second compartment generally defined between at least the third sheet and the first outer sheet. Fluid flow means are positioned between the third sheet and the second sheet. The fluid means comprises a first end extending into a first side of the first compartment and a second end extending into a second side of the first compartment. The fluid means includes a plurality of perforations in communication with the first compartment. The fluid bag further comprises means for selectively expanding the second compartment to exert force on at least a portion of the first compartment so as to control the rate of flow of fluid through the fluid means. Preferably, the first and second sheets are substantially square. The first and second sheets are preferably joined at a first seal, and the third sheet and the second sheet are preferably joined at a second seal inwardly of the first seal. The first and second ends of the fluid means preferably extend into opposed sides of the first compartment. Each of the sheets is preferably formed of PVC.

The invention further provides an apparatus for reinfusing fluid to a patient comprising a fluid collection device for receiving fluid from a patient and a fluid bag being in fluid communication with the fluid collection device so that the fluid from the patient can selectively pass to the fluid bag. The fluid bag comprises a first expandable compartment for containing at least a portion of the fluid to be collected and transferred and fluid means for allowing fluid to flow selectively into and out from the chamber, the fluid means including at least one perforation in fluid communication with the first compartment. The bag further comprises means for changing the pressure of the fluid in the compartment and pressure source means fluidly coupled to the pressure changing means, wherein the pressure source means can be selectively activated to exert force on at least a portion of the first compartment to control the rate of flow of fluid to the patient.

In another aspect of the invention, a method of reinfusing fluid to a patient comprises draining a portion of fluid collected from the patient into a fluid bag. The fluid bag comprises an expandable compartment for containing at least a portion of the fluid to be collected and transferred and fluid means for allowing fluid to flow selectively into and out from the compartment, the fluid means including at least one perforation in fluid communication with the compartment. The fluid bag further comprises means for changing the pressure of the fluid in the compartment wherein the pressure changing means exerts force on at least a portion of the exterior surface of the compartment. The method includes changing the pressure of the fluid in the compartment so as to regulate the flow of fluid through the fluid means.

DETAILED DESCRIPTION OF THE INVENTION

In the description which follows, any reference to either orientation or direction is intended primarily for the purpose of illustration and is not necessarily intended in any way as a limitation of the scope of the present invention.

Figure 1:
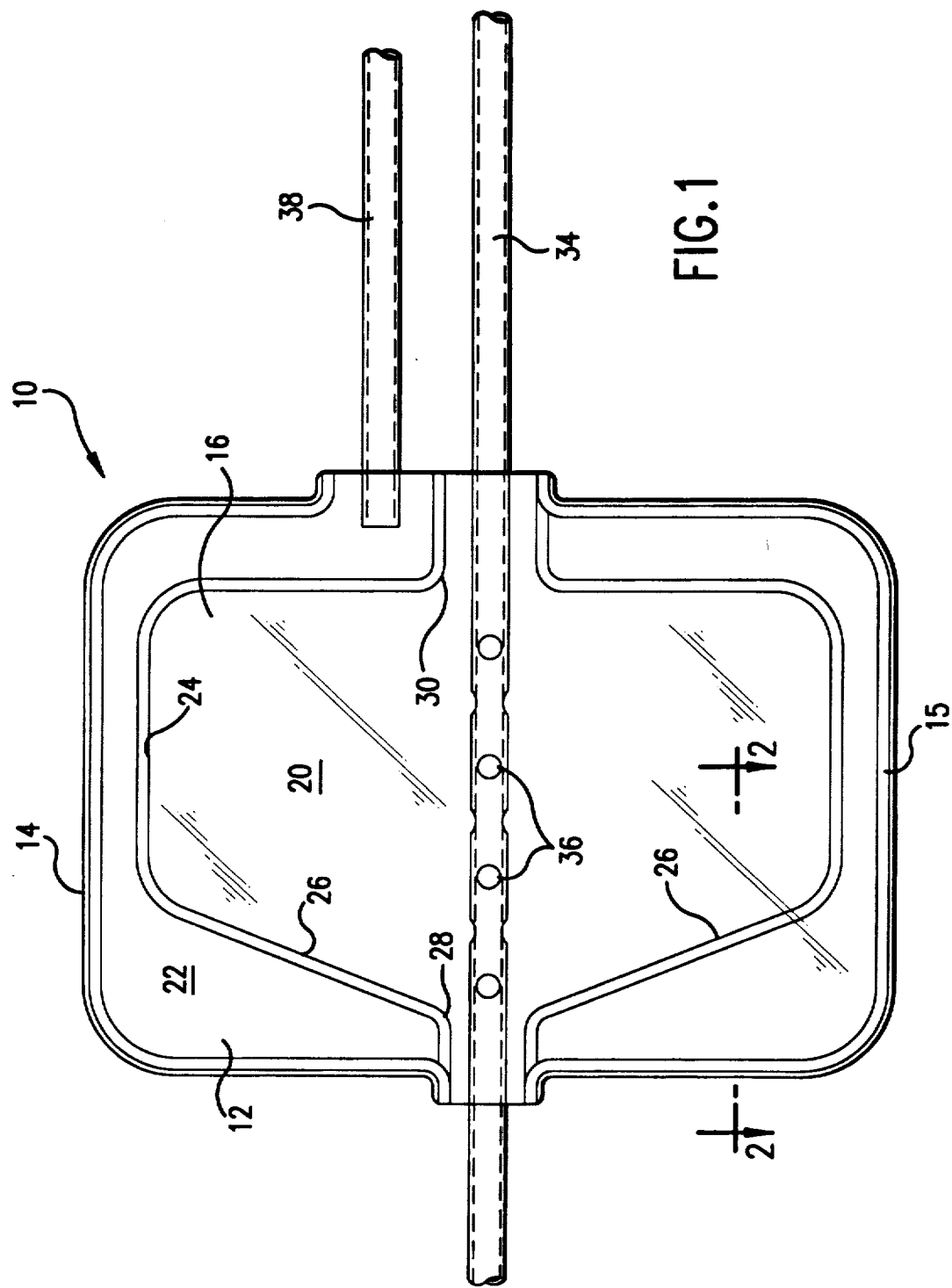
FIG. 1 is a top plan view of a blood transfer bag in accordance with the present invention.
Figure 2:
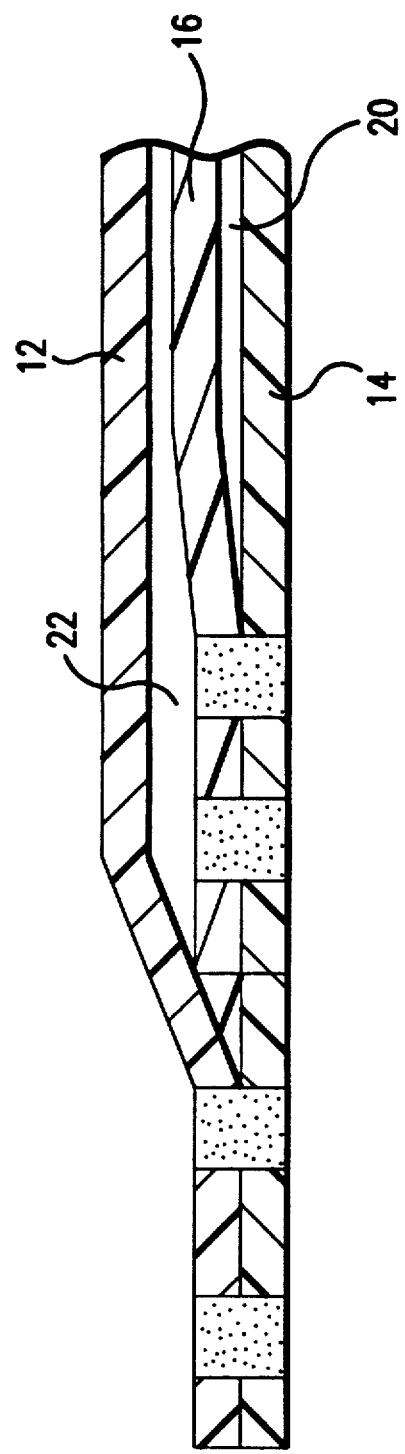
FIG. 2 is an enlarged partial side view of the transfer bag taken along line 2—2 of FIG. 1.

Referring to FIGS. 1 and 2, a transfer bag 10 in accordance with the present invention has first and second sheets 12, 14 that define the outer walls of the transfer bag 10. The sheets 12, 14 are joined along their edges at a seal line 15. The bag 10 further includes a third or inner sheet 16 positioned between the first and second sheets 12, 14 and joined to at least one of the outer sheets, such as the second sheet 14 as shown in FIG. 2.

As further illustrated in FIG. 2, a first compartment or chamber 20 that is expandable or inflatable is defined in the bag 10 between the inner sheet 16 and the second outer sheet 14. A second compartment or chamber 22 that is also expandable or inflatable is formed between the first and second outer sheets 12, 14 and the inner sheet 16. Referring now to FIGS. 1 and 2, the sheets 12, 14, 16 are preferably generally square or trapezoidal and are formed of a flexible material, such as polyvinylchloride (PVC). Preferably, the third sheet 16 is joined to the second sheet 14 along a seal line 24, inward of the seal line 15 joining the first and second sheets 12, 14. If desired, sheet 16 can be of the same general shape and configuration as sheets 12 and 14. In that event, seal lines 15 and 24 would overlap. The seal line 24 joining the second and third sheets 14, 16 includes angled portions 26 forming a first neck portion 28 in the first compartment 20. The seal 24 further forms a second neck portion 30 in the first compartment 20, opposite the first neck portion 28. The sheets 12, 14, 16 can be joined to one another in accordance with conventional RF welding techniques. Those skilled in the art will appreciate that many other sheet configurations, sheet materials, and methods of attachment are possible, depending upon the desired application of the transfer bag 10.

A first tube 34 is positioned in openings in the neck portions 28, 30 of the first compartment 20, extending longitudinally therethrough. The first tube 34 includes perforations 36 so as to be in fluid communication with the first compartment 20. A second tube 38 is positioned in an opening between the first and second sheets 12, 14 so as to be in fluid communication with the second compartment 22 defined therebetween. As will be explained in more detail below, the first compartment 20 acts as a transfer compartment or chamber for receiving, storing and/or transferring fluid to be reinfused to a patient. The second compartment 22 serves as a pressure compartment or chamber which may be selectively inflated to at least accelerate the reinfusion process if desired.

Figure 3:
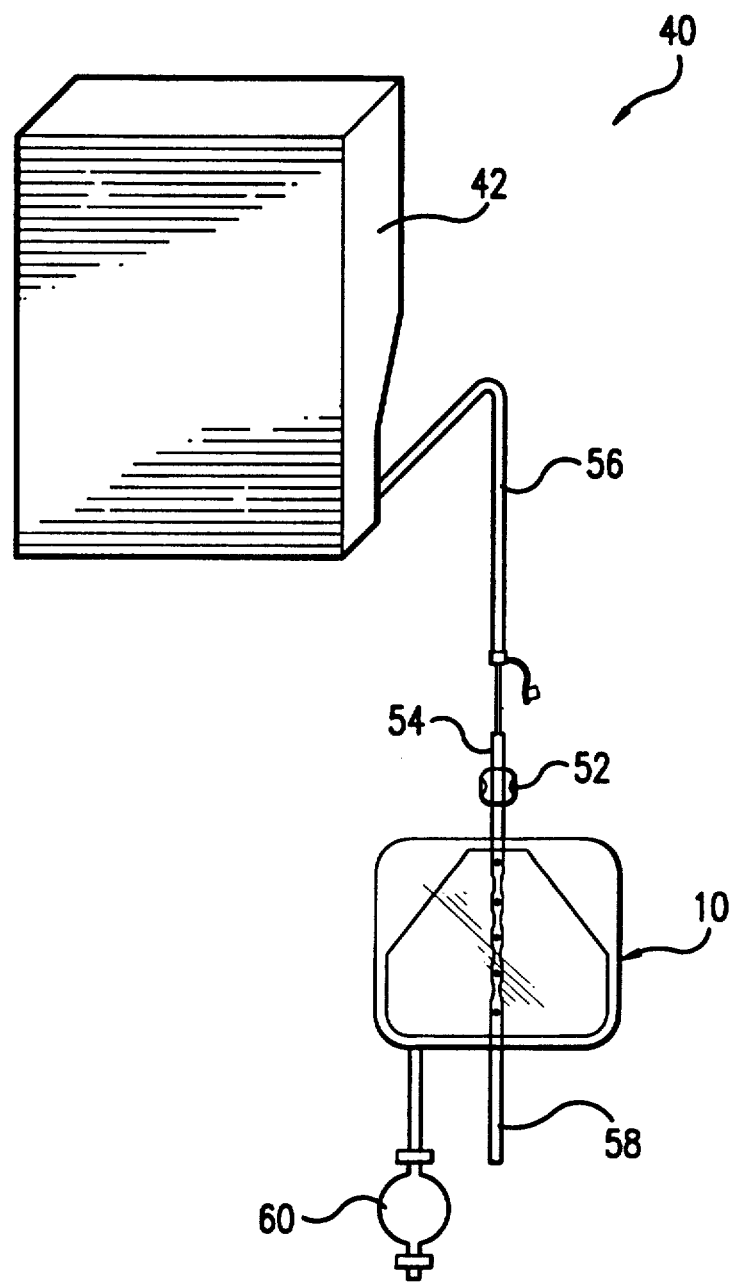
FIG. 3 illustrates the transfer bag incorporated in a reinfusion system.

FIG. 3 illustrates one particular application of the transfer bag 10 as incorporated within a preferred embodiment of a reinfusion system 40. The system 40 includes a blood or fluid collection device 42, such as the Pleur-evac ® Plus A-9250 which is available from Deknatel, Inc. The collection device 42 can be preferably either a chest drainage device or a cardiotomy reservoir, each of which defines a chamber into which blood and/or fluid can be collected and/or aspirated from a wound site and subsequently reinfused to a patient.

In operation, blood and/or fluid from the wound site is preferably pulled by vacuum in a known manner into the collection chamber of device 42. A conventional clamp 52 may be placed between the device 42 and transfer bag 10 to regulate fluid flow therebetween. When appropriate or desired, blood which has been collected in the chamber of device 42 can be reinfused to a patient via the transfer bag 10. The transfer bag 10 can be positioned vertically so that the first neck portion 28 of the first compartment 20 is located at a top end of the bag 10 and the second neck portion 30 is located at a bottom end of tile bag 10. In this position, the tubes 34, 38 extend vertically through the respective openings in the bag 10. In particular, a first end 54 of the transfer tube 34 is connected to the device 42 of the reinfusion system 40 via a tube 56 such that the transfer tube 34 is in fluid communication with the chamber of device 42, and a second end 58 of the transfer tube 34 is connected to a line (not shown) which provides fluid to a patient.

In accordance with one preferred embodiment of the invention, the transfer bag 10 can provide a simple and effective air purge. To remove air from the transfer bag 10 prior to initiating fluid flow, the line connected between the transfer tube and the patient is temporarily clamped in a well-known manner. The bag 10 is then squeezed, thereby forcing any air contained in the fluid transfer chamber 20 through the openings in the perforated tube 34. The tube 34 conducts the air from the transfer chamber 20 to the chamber of device 42 where conventional means provide for removal of air from the reinfusion system 40. Thus, the perforated tube 34 extending through the transfer chamber 20 directs air out of the chamber without any further manipulation by the operator, increasing efficiency and reducing time spent by medical personnel setting up the reinfusion system 40. Those skilled in the art will further appreciate that with the design of the present invention, air can be removed from the transfer chamber 20 via the perforated tube 34 when the transfer bag 10 is in any position, and is not limited to the vertical position illustrated in FIG. 3.

When desired, collected blood is selectively allowed to flow from the device 42 under the action of gravity through the transfer tube 34 and into the fluid transfer compartment 20 of the transfer bag 10 by opening the clamp 52 between the device 42 and transfer bag 10. The blood flowing into the bag 10 through the transfer tube 34 can collect in the first or transfer compartment 20 of the bag. Of course, if the bag 10 is situated above the patient, this flow of blood into the bag can also be accompanied by some flow out of the bag and to the patient. If situated below the patient, blood will only flow into the bag. Optimal flow occurs when the vacuum within the device 42 is removed.

When the transfer compartment 20 is sufficiently full, the user can close the clamp 52 between the bag 10 and the device 42 and open the clamp on the line between the bag and the patient, thereby permitting flow between the bag and the patient. For standard or typical reinfusion, the blood in the transfer compartment 20 will exit the bag 10 through the transfer tube 34 and be reinfused to the patient through a catheter or needle (not shown) in a conventional manner. The rate of reinfusion when operated in this manner is approximately the same as if the bag 10 were not present. However, the volume capacity of the reinfusion system 40 is greater with the transfer bag 10 than with the device 42 alone, enabling larger amounts of blood to be collected and reinfused.

If a faster rate of reinfusion is desired, the transfer tube 34 may be clamped using the clamp 52 positioned between the device 42 and transfer bag 10 as illustrated to temporarily cease flow into the transfer compartment 20 from the device 42. The pressure compartment 22 is then inflated in a conventional manner, for example, by using a pressure bulb 60. When inflated via the pressure tube 38, the pressure compartment 22 expands, forcing fluid out of the transfer compartment 20 through the transfer tube 34 to accelerate the reinfusion of the fluid collected in the transfer chamber. Once the reinfusion of the fluid has been completed, pressure through tube 38 can be released, and the clamp 52 can be reopened to again permit the flow of blood from the device 42 to the transfer compartment 20 in the bag 10. Pressurization of the transfer bag 10 in this manner also permits reinfusion of fluid collected in the transfer chamber 20 when the transfer bag is situated below the patient. After the pressure chamber 22 has been inflated, fluid within the transfer chamber 20 can be pumped "uphill" to the patient via the transfer tube 34 and catheter or needle connected to the line coupled to the second end 58 thereof.

Thus, the present invention effectively provides for an increase of both the volume and rate of fluid transfer. In addition, the transfer bag 10 of the present invention provides safety precautions when blood or other fluids posing risks to medical personnel are to be transferred. The configuration of the seals 15, 24 joining the flexible sheets 12, 14, 16 which form the transfer and pressure compartments 20, 22 in the bag 10 ensures that if the seal 24 between the second sheet 14 and third sheet 16 is broken at any given point, the contents of the transfer compartment 20 will leak into the pressure compartment 22 and not leak outside the transfer bag 10, substantially decreasing the risk of attending medical personnel coming into contact with the patient's fluid such as blood. The flow-through tube 34 in communication with the transfer compartment 20 further minimizes or helps to eliminate the risks associated with connecting and disconnecting multiple tubes to the transfer bag 10.

Figure 4:
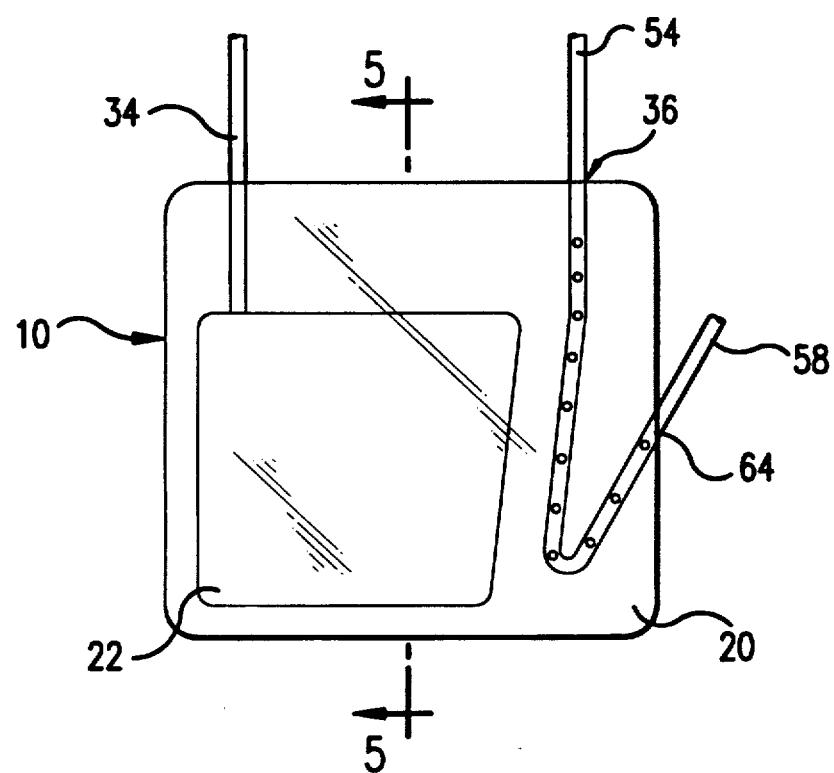
FIG. 4 illustrates an alternative embodiment of the blood transfer bag in accordance with the present invention.
Figure 5:
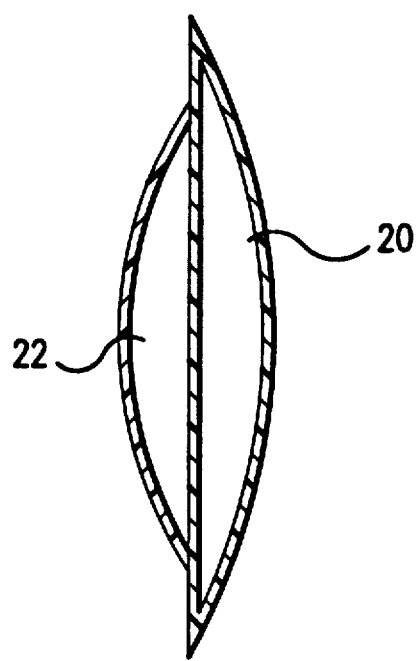
FIG. 5 is a side cross-sectional view taken along line 5—5 of FIG. 4.

It will appreciated that although a preferred configuration of the transfer bag 10 has been illustrated herein, several variations and modifications would be apparent to those skilled in the art. For example, the transfer tube 34 need not necessarily extend through the transfer chamber 20 as in FIG. 1. Rather as illustrated in the alternative embodiment of FIG. 4, the second end 58 of the transfer tube 34 can curve or bend within the chamber 20 and extend through an outlet 64 provided in any other side of the bag 10. Further, as illustrated in FIGS. 4 and 5, the pressure compartment 22 can be of a smaller volume than the transfer compartment 20.

Other variations of the above-described transfer bag 10 which involve minor changes are clearly contemplated to be within the scope of the present invention. These modifications and variations may be made without departing from the spirit and scope of the present invention, as will become apparent to those skilled in the art. The specific embodiments described herein are offered by way of example only, and the invention is set forth in the appended claims.

What is claimed is:

1. Apparatus for collecting and transferring fluid therefrom, comprising:
    a first expandable compartment for containing at least a portion of the fluid to be collected and transferred;
    a fluid flow means extending continuously into and out from said first expandable compartment, said fluid flow means comprising a first end extending into said first expandable compartment at a first location, and a second end fluidly coupled to said first end and extending out of said first expandable compartment at a second location, said fluid means including at least one perforation in fluid communication with said first expandable compartment for allowing said fluid to flow selectively into and out from said compartment; and
    means for changing the pressure of the fluid in said compartment, wherein said pressure changing means exerts force on at least a portion of said first compartment to aid in regulating the flow of fluid through said fluid means.

2. Apparatus according to claim 1 wherein said fluid means comprises a tube having a plurality of perforations in fluid communication with said first compartment.

3. Apparatus according to claim 1 wherein said pressure changing means comprises a second expandable compartment adjacent said first expandable compartment.

4. Apparatus according to claim 3 further comprising pressure source means in communication with said second compartment.

5. A fluid bag comprising:
    first and second sheets joined along edges thereof to define outer walls of said bag;
    a third sheet disposed between said first and second sheets and joined to at least portions of said second sheet, wherein said third sheet separates the space defined between said first and said second outer sheets into a first expandable compartment and a second expandable compartment, said second expandable compartment generally defined between at least said third sheet and said first sheet, and said first expandable compartment generally defined between said third sheet and said second sheet;
    a fluid flow means positioned between said third sheet and said second sheet and extending continuously through said first expandable compartment, said fluid means comprising a first end extending into a first side of said first compartment, and a second end fluidly coupled to said first end and extending into a second side of said first compartment, said fluid means including a plurality of perforations in communication with said first compartment so as to allow said fluid to flow selectively into and out from said first compartment; and
    means for selectively expanding said second compartment to exert force on at least a portion of said first compartment so as to control the rate of flow of fluid through said fluid flow means.

6. The fluid bag according to claim 5 wherein said first and said second sheets are substantially square.

7. The fluid bag according to claim 5 wherein said first and said second sheets are joined at a first seal, and wherein said third sheet and said second sheet are joined at a second seal inwardly of said first seal.

8. The fluid bag according to claim 7 wherein said first and second ends of said fluid means extend into opposed sides of said first compartment.

9. The fluid bag according to claim 5 wherein each of said sheets are formed of PVC.

10. Apparatus for reinfusing fluid to a patient comprising:
    a fluid collection device for receiving fluid from a patient;
    a fluid bag being in fluid communication with said fluid collection device so that the fluid from the patient can selectively pass to said fluid bag, said fluid bag comprising:

an expandable compartment for containing at least a portion of the fluid to be collected and transferred;

a fluid flow means extending continuously into and out from said expandable compartment, said fluid flow means comprising a first end extending into said first expandable compartment at a first location, and a second end fluidly coupled to said first end and extending out of said first expandable compartment at a second location, said fluid means including at least one perforation in fluid communication with said expandable compartment for allowing said fluid to flow selectively into and out from said compartment; and means for changing the pressure of the fluid in said compartment; and pressure source means fluidly coupled to said pressure changing means, wherein said pressure source means can be selectively activated to exert force on at least a portion of said first compartment to control the rate of flow of fluid to the patient.

11. A method of reinfusing fluid to a patient comprising:

draining a portion of fluid collected from the patient into a fluid bag, said fluid bag comprising an expandable compartment for containing at least a portion of the fluid to be collected and transferred and a fluid flow means extending continuously into and out from said expandable compartment, said fluid flow means comprising a first end extending into said first expandable compartment at a first location, and a second end fluidly coupled to said first end and extending out of said first expandable compartment at a second location, said fluid means including at least one perforation in fluid communication with said expandable compartment for allowing said fluid to flow selectively into and out from said compartment, said fluid bag further comprising means for changing the pressure of the fluid in said compartment, wherein said pressure changing means exerts force on at least a portion of the exterior surface of said compartment;

changing the pressure of fluid in said compartment so as to regulate the flow of fluid through said fluid means.

* * * * *